United States Patent [19]

Rosenstatter

[11] Patent Number: 5,476,380
[45] Date of Patent: Dec. 19, 1995

[54] DENTAL HANDPIECE

[75] Inventor: Otto Rosenstatter, Seeham, Austria

[73] Assignee: Imtec Innovative Medizintechnik Gesellschaft m.b.H., Hallein, Austria

[21] Appl. No.: 204,332

[22] PCT Filed: Aug. 6, 1992

[86] PCT No.: PCT/AT92/00109

§ 371 Date: Mar. 14, 1994

§ 102(e) Date: Mar. 14, 1994

[87] PCT Pub. No.: WO93/05723

PCT Pub. Date: Jan. 4, 1993

[30] Foreign Application Priority Data

Sep. 13, 1991 [AT] Austria .................................. 1839/91
Dec. 6, 1991 [DE] Germany ............................ 9115190 U

[51] Int. Cl.⁶ .............................. A61C 1/07; A61C 3/03;
A61C 3/08; A61C 1/02
[52] U.S. Cl. ........................... 433/100; 433/120; 433/132
[58] Field of Search .................................. 433/100, 120,
433/126, 132

[56] References Cited

U.S. PATENT DOCUMENTS

| 3,439,422 | 4/1969 | Doeden et al. |
|---|---|---|
| 4,021,919 | 5/1977 | Lingenhöle et al. |
| 4,040,311 | 8/1977 | Page, Jr. et al. ..................... 433/120 X |
| 4,266,934 | 5/1981 | Pernot ................................. 433/100 X |
| 4,278,427 | 7/1981 | Lingenhole et al. ..................... 433/100 |
| 4,382,786 | 5/1983 | Lohn et al. ........................... 433/100 X |
| 4,403,958 | 9/1983 | Löhn . |
| 4,504,227 | 3/1985 | Lohn ................................... 433/132 X |
| 4,534,734 | 8/1985 | Lares ..................................... 433/126 |
| 4,642,051 | 2/1987 | Lohn ..................................... 433/100 |
| 5,286,194 | 2/1994 | Horiuchi et al. ........................ 433/132 |

FOREIGN PATENT DOCUMENTS

| 377176 | 2/1985 | Austria . |
|---|---|---|
| 2440184 | 5/1980 | France . |
| 3009337 | 9/1981 | Germany . |
| 3407902 | 12/1982 | Germany . |
| 558170 | 1/1975 | Switzerland . |
| 668696 | 1/1989 | Switzerland . |
| 2042081 | 9/1980 | United Kingdom . |

Primary Examiner—Nicholas D. Lucchesi
Attorney, Agent, or Firm—Wenderoth, Lind & Ponack

[57] ABSTRACT

A dental handpiece includes an end grip member gripped by an operator during use. The end grip member has a first end to be connected to an air supply and a second end on which is selectively detachably mounted a tool holder supporting a tool that is driven either by a mechanical structure or by an air turbine, depending upon the particular tool holder mounted on the end grip member. Within the end grip member is an air motor, and a first air line extends from the first end to the air grip motor. When the tool holder includes the mechanical structure, then the first air line supplies air to the air motor, thereby to transmit power to the mechanical structure. A second air line extends through the end grip member between the first and second ends thereof. When the particular tool holder mounted on the end grip member includes an air turbine, the second air line supplies air thereto. An adjusting mechanism is mounted on the end grip member to selectively open one of the first and second air lines while closing the other of the second and first air lines.

14 Claims, 4 Drawing Sheets

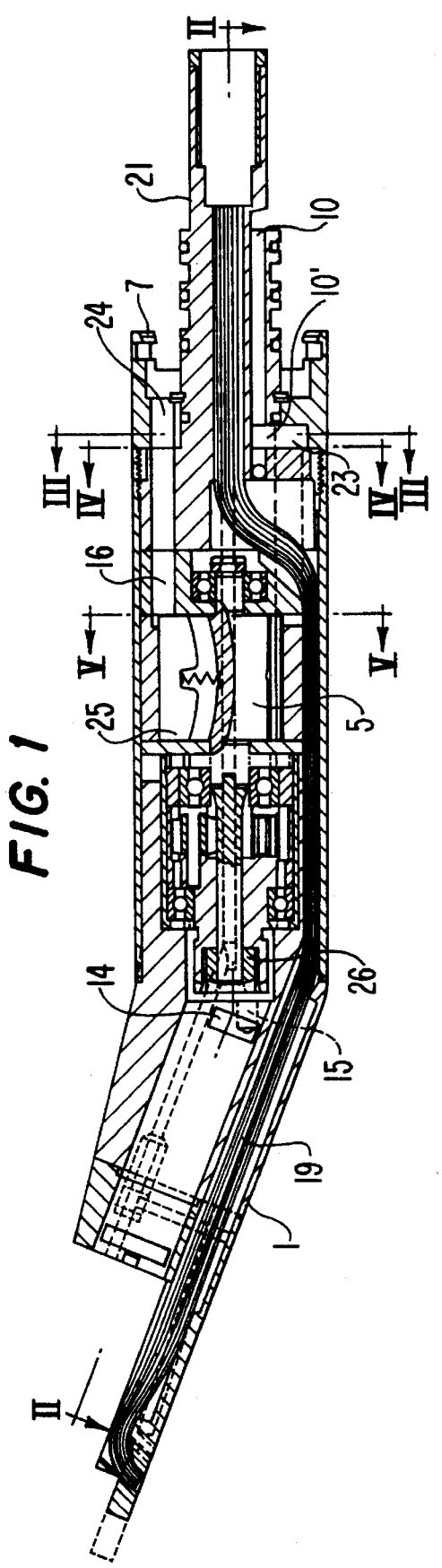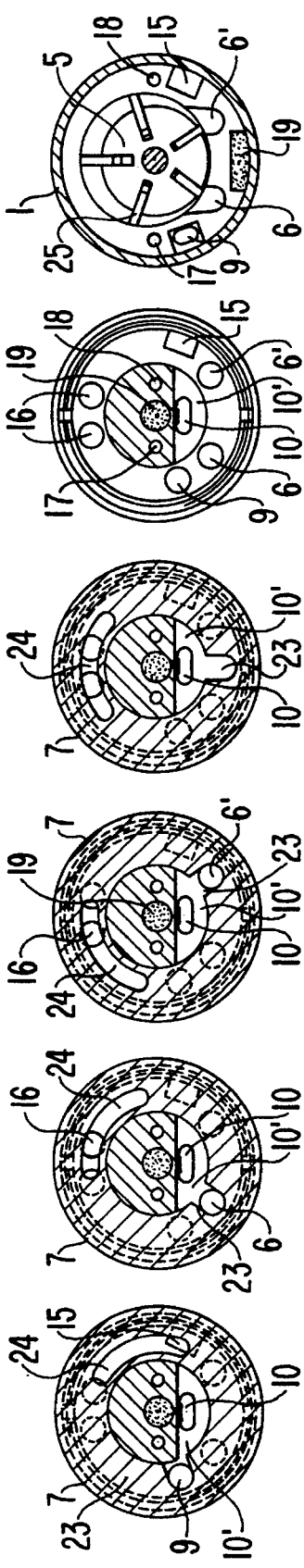

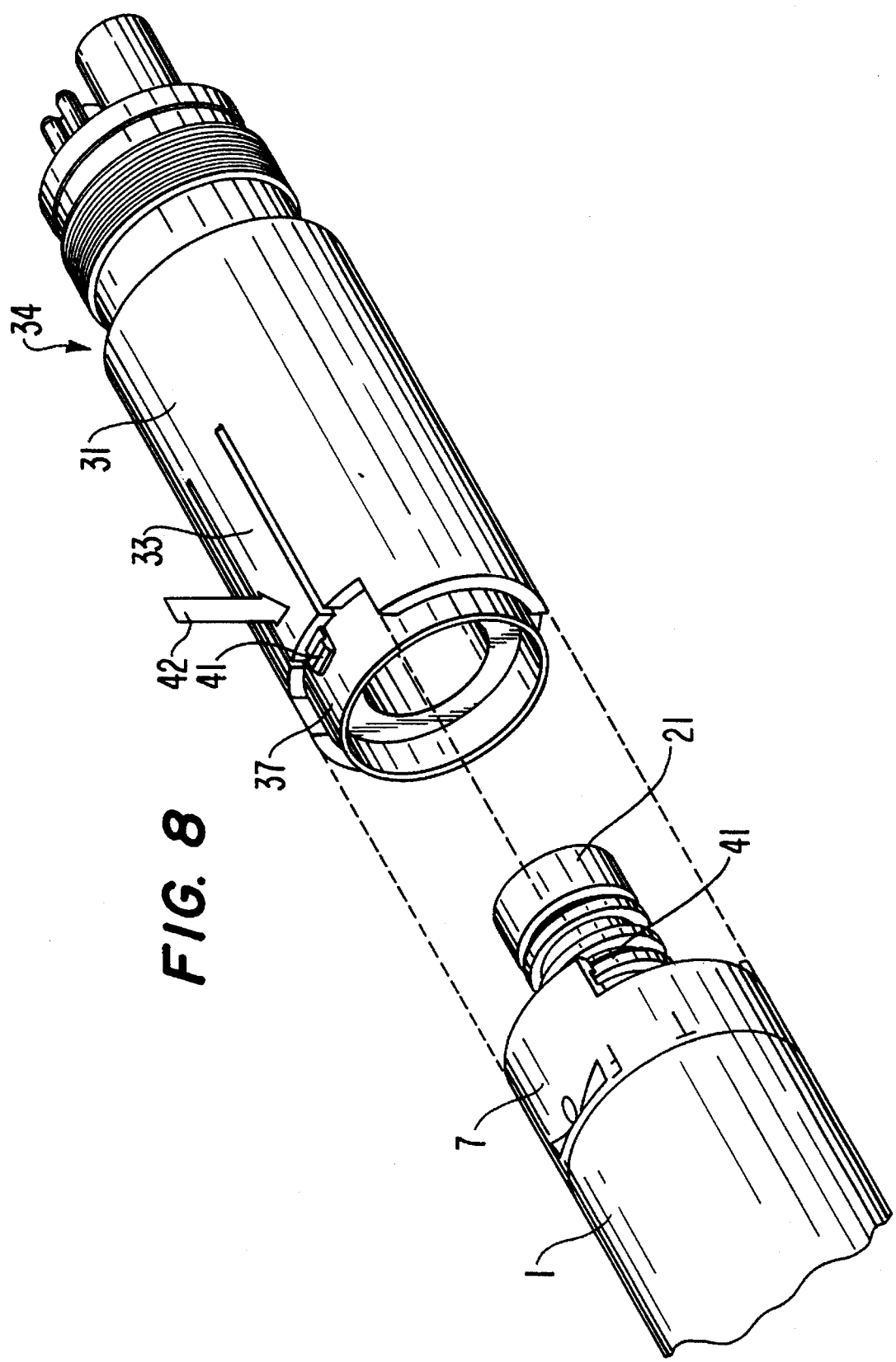

DENTAL HANDPIECE

BACKGROUND OF THE INVENTION

The invention relates to a dental handpiece comprising an end grip member or handle to be gripped by a user and which contains a motor to which leads a propellant air line the flow to which is controlled by means of an adjusting ring mounted on the end grip member, and a headpiece which can be removably attached by way of a neck piece to the end grip member and which carries a rotating tool.

Such handpieces are known, for example, from AT-A-347 013 and DE 30 09 337. The motor disposed in the end grip member is designed as a pneumatic motor and includes blades, a sleeve-shaped housing forming a stator, and a rotor which is located in the housing and having an axis of rotation extending parallel to an axis of a circular cylindrical inner wall of the housing and offset relative thereto. At least one air inlet port for compressed air and at least one air outlet port open into a space between the rotor and the circular cylindrical inner wall. When compressed air is admitted into the motor, the compressed air flows through the air inlet port(s) into the space between rotor and circular cylindrical inner wall and pushes in front of it a blade that projects the furthest beyond the rotor, so that the rotor begins to rotate, and then the next blade is impinged on by the compressed air.

A range of velocity that can be obtained with such a device lies between 0 and 40,000 rpm, for which the technical term is the low speed range. A desired speed is set by means of an adjusting ring, which, starting from a zero position, can be set to different fast clockwise rotation or to counter-clockwise rotation positions. For higher speeds, either a mechanical drive or a turbine with an air drive, which immediately envelope the rotating tool (cf. AT-A 344 875) is used conventionally. Such turbines are to be operated in a speed range of 200– 350,000 rpm.

According to the current state of the art, if a change is made from a handpiece with a drive in the end grip member to a handpiece with head turbine, the end grip member is changed. This means not only a certain time-consuming manipulation, but also increased costs due to a larger number of end grip members that must be kept on hand.

SUMMARY OF THE INVENTION

In contrast, the object of the invention is to provide an end grip member or handle that is as universal as possible. This object is achieved according to the invention in that the end grip member includes an additional propellant air line which runs to a point of attachment between the end grip member and the neck piece and that propellant air can be introduced by choice into one of the two propellant air lines by means of an adjusting mechanism.

Such arrangement makes it possible to manage with a smaller number of end grip members than before, thus justifying for the first time designing the end grip member in a relatively complicated manner, for example, by disposing expensive optical systems therein.

It is provided in an advantageous manner that the adjusting mechanism is designed as an adjusting ring that is connected rigidly to a sleeve which is mounted rotatably on a connecting member. With this arrangement it is achieved that under constant operating conditions the entire region of the handpiece that is enveloped by the physician's hand remains unaffected by rotations of a supply hose. In contrast, changes in speed and direction of rotation are readily possible, since the adjusting ring is more than adequately wide due to its connection to the sleeve enveloping the connecting member. A special advantage lies in the fact that the adjusting ring, which is necessary in any event, can also furnish together with the sleeve the coupling between connecting member and end grip member, which can be constructed, for example, with elastic flexible tongues. If it is provided that the connecting member terminates in a pipe which envelops a cone attached to the end grip member, there is the possibility of making the sleeve enveloping the connecting member and the tongues, provided as coupling means, relatively thin since they are braced against the connecting member.

BRIEF DESCRIPTION OF THE DRAWINGS

Other details of the invention are explained in the following with reference to the drawings, wherein:

FIG. 1 is a vertical longitudinal view of an end grip member or handle of a dental handpiece that is designed according to the invention;

FIGS. 3a–3d are sectional views showing different positions of an adjusting ring and taken along line III—III of FIG. 1;

FIG. 4 is a sectional view taken along line IV—IV of FIG. 1;

FIG. 5 is a sectional view taken along line V—V of FIG. 1;

FIG. 8 is a perspective view depicting a region of attachment of the end grip member with a connecting member.

DETAILED DESCRIPTION OF THE INVENTION

Figure 2:
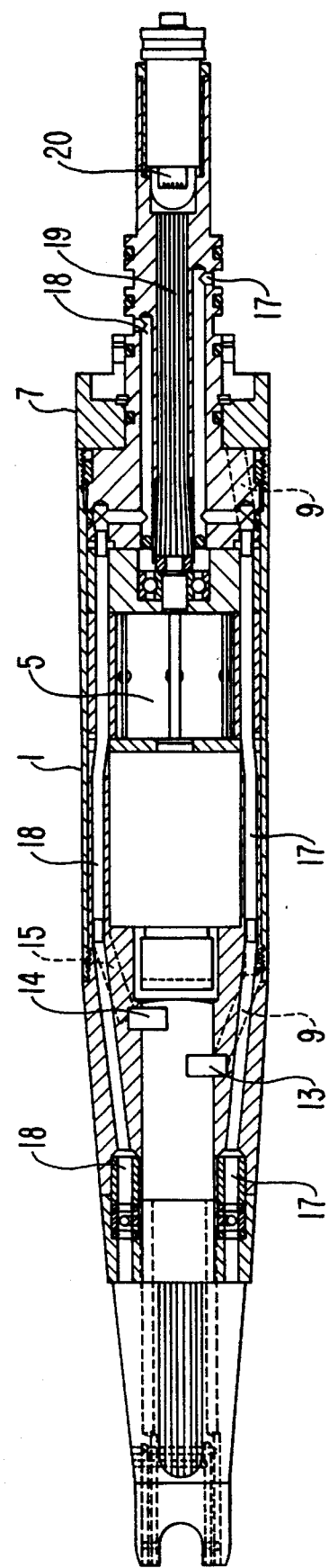
FIG. 2 is a sectional view of the handpiece of FIG. 1 taken along line II—II in FIG. 1.

FIG. 1 depicts an end grip member or handle 1 of a dental handpiece, which, on the one hand (on the right in the drawing) can be connected to a connecting member for supply lines of propellant air, cooling water, cooling air, etc. and, on the other hand, can be connected to an interchangeable tool holder. The end grip member 1 contains a motor 5 which can drive by way of a gear 26 a drive shaft extending in the usual manner through a neck piece of a tool holder. This motor 5 is preferably a bladed motor of the kind shown in FIG. 5, in which a rotor, which rotates on a central axle in an eccentric bore, is equipped with radially slidable, spring-loaded blades 25. The direction of rotation of the rotor depends on whether propellant air is supplied through inlet 6 and then is discharged at 6' or whether the air is supplied through the line 6' and discharged through the line 6.

Figure 7:
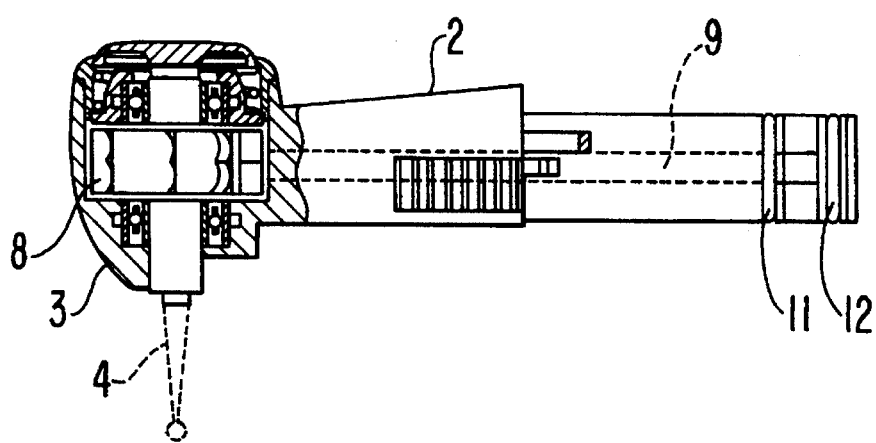
FIG. 7 is a partially sectional view depicting a tool holder that can be connected to the end grip member of FIGS. 1 and 2 and that comprises a neck piece portion and a headpiece portion.

As explained in detail further below, a tool can be driven when the motor 5 is standing still by feeding propellant air through the end grip member 1 to a turbine 8 which is disposed in a headpiece or head member 3 of the tool holder that includes headpiece 3 and a neck piece or member 2 for a tool 4 (see FIG. 7).

Figure 6:
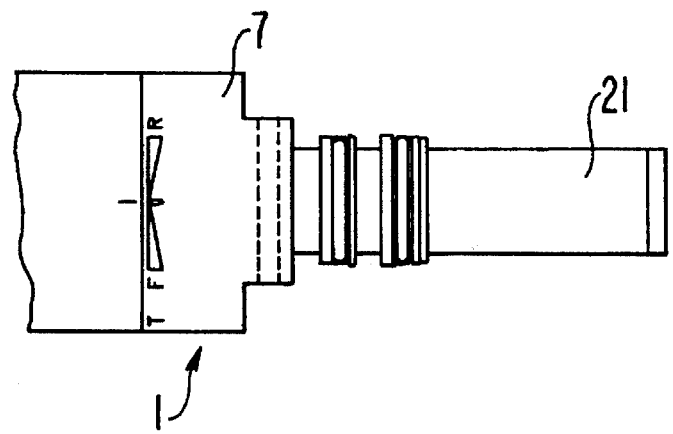
FIG. 6 is a side view of an attachment end of the end grip member.

An adjusting ring 7, which can be rotated on a cone or coupling 21 of the end grip member 1 and as shown in FIG. 6, serves to switch between individual types of drives. In a position T of ring 7, the turbine 8 is driven. In positions F and R of ring 7, the motor 5 is driven in opposite directions. Position 0 is a neutral position. The function of the adjusting ring 7 is evident from FIGS. 3a–3d. The adjusting ring 7 has therein a radial expansion 23 of a central bore, in order to open a propellant air inlet. Ring 7 further has a tangentially extending oblong slot 24 for return air. Propellant air flows to the expansion 23 of the adjusting ring 7 through feed line 10 in the coupling 21. An inner end of line 10 expands into a recess 10' which has the shape of a segment of a circle and communicates with the expansion 23 of the adjusting ring 7.

FIG. 4 shows altogether the possibilities that can be selected. The propellant air can be fed by choice through the line 6 or the line 6' to the motor 5 and can be led back over the return lines 16 or can be guided via propellant air line 9 to the turbine 8 and can flow back to the return line 15. In addition to the aforementioned propellant air lines, the end grip member 1 also contains a cooling water line 19, the details of which will be explained below. To facilitate comprehension, the joint propellant air feed line 10 and the recess 10' are also projected on the plane of FIG. 4. Such joint propellant air feed line and recess are located on the right of plane IV—IV in FIG. 1.

FIGS. 3a–3d show in detail how a desired choice between the different types of drives can be made by rotating the adjusting ring 7. In the position according to FIG. 3a, the expansion 23 of the adjusting ring 7 releases the propellant air line 9. As is apparent from FIG. 2, the propellant air flows through line 9 to a recess 13, which terminates between O-rings 11 and 12 of the tool holder shown in FIG. 7, so that the propellant air line 9 continues as far as the turbine 8. The return air flows through a line, which in FIG. 7 is covered by the propellant air line 9 and which terminates on the front side of the neck piece 2 to the right of the O-ring 12. When the tool holder is assembled, O-ring 12 is between recesses 13, 14 so that the return air flows in the recess 14 and from there into the line 15, which is released by the oblong slot 24 in the position according to FIG. 3a.

In the position of the adjusting ring 7 according to FIG. 3b, the propellant air line 6 which leads to the motor 5 is released. At the same time the return air can flow out through one of the lines 16 through the oblong slot 24 in the adjusting ring 7. In the position according to FIG. 3c, the propellant air line 6' is released and the direction of rotation of the motor 5 reverses. In the position according to FIG. 3d the propellant air is shut off.

In addition to the propellant air lines, the alternative admission to which is the subject matter of the invention, the end grip member 1 has other lines which are briefly described below, since the design thereof is a prerequisite for the practical application of the invention. Thus, light line 19 for light supplied from a light source 20 runs on the underside of the end grip member 1. On the left side of the end grip member 1 extends cooling water line 17, and on the right side thereof extends cooling air line 18. These lines continue as far as the tip of the end grip member 1, where such lines branch and cross, so that a cooling spray is formed in the conventional manner.

The arrangement of the adjusting ring 7 on the end of the end grip member 1, as is especially evident from FIG. 8, is advantageous. The adjusting ring 7 can be connected to a sleeve 31 of a connecting member 34, since the adjusting ring 7 and tongues 33 of sleeve 31 have corresponding stop members 41 that produce a connection between the adjusting ring 7 and the sleeve 31 when the parts 34 and 1 are slid together. This connection is achieved by depression of tongues 33, as indicated by the arrow 42. Connecting member 34 envelops a pipe 37, which receives cone 21 of the end grip member 1. Thus, sleeve 31 can be made with relatively thin walls, since the pipe 37 ensures the stability of the connection member 34. The cone 21 can be rotated in the pipe 37, whereby annular grooves arranged between seals at the cone 21 make it possible for the supplied media to pass into the end grip member 1.

In the embodiment of the adjusting ring 7 shown in FIG. 8, the assumption was made that propellant air, which can be led by choice to the turbine 8 (T) or to the air motor 5 (F-0-R), flows in a manner according to the invention through the end grip member. However, this measure is also applicable if the adjusting ring 7 controls an electric motor.

I claim:

1. A dental handpiece comprising:

an end grip member to be gripped by an operator during use, said end grip member having a first end to be connected to an air supply and a second end;

at least one tool holder selectively connectable to and detachable from said second end of said end grip member, said tool holder including means for driving a tool to be carried by said tool holder;

an air motor within said end grip member;

a first air line extending from said first end of said end grip member to said motor to, when said end grip member is connected to the air supply, convey air to said air motor to operate said driving means;

a second air line extending through said end grip member from said first end thereof to said second end thereof to, and when said end grip member is connected to the air supply, convey air to said driving means; and an adjusting mechanism on said end grip member which selectively opens one of said first air line or said second air line while closing the other of said second air line or said first air line.

2. A dental handpiece as claimed in claim 1, wherein said adjusting mechanism comprises an adjusting ring mounted on said end grip member for rotation relative thereto.

3. A dental handpiece as claimed in claim 2, further comprising a connecting member rotatably connected to said first end of said end grip member and to be connected to the air supply, and a sleeve rotatably mounted on said connecting member and rigidly connected to said adjusting ring.

4. A dental handpiece as claimed in claim 3, wherein the rigid connection between said sleeve and said adjusting ring is formed by a detachable connecting structure therebetween.

5. A dental handpiece as claimed in claim 4, wherein said connecting structure includes elastic flexible tongues formed on said sleeve.

6. A dental handpiece as claimed in claim 3, wherein said connecting member includes a pipe enveloping a cone attached to said end grip member.

7. A dental handpiece as claimed in claim 1, wherein said driving means comprises a mechanical means and wherein said air motor transmits power to said mechanical means.

8. A dental handpiece as claimed in claim 1, wherein said driving means comprises an air turbine means and wherein said second air line conveys air to said air turbine means.

9. An end grip member to form part of a dental handpiece and to be gripped by an operator during use of the dental handpiece, said end grip member comprising:

a first end to be connected to an air supply;

a second end to have selectively detachably connected thereto at least one tool holder carrying a tool operable by mechanical means or air turbine means of the tool holder;

an air motor;

a first air line extending from said first end to said motor to, when the tool holder includes the mechanical means and when said first end is connected to the air supply, convey air to said air motor to operate said air motor and thereby transmit power from said end grip member to the mechanical means of the tool holder;

a second air line extending from said first end to said second end to, when the tool holder includes the air turbine means and when said first end is connected to the air supply, convey air from said second end of said end grip member to the air turbine means of the tool holder; and an adjusting mechanism for selectively opens one of said first air line or said second air line while closing the other of said second air line or said first air line.

10. An end grip member as claimed in claim 9, wherein said adjusting mechanism comprises an adjusting ring mounted on said end grip member for rotation relative thereto.

11. An end grip member as claimed in claim 10, further comprising a connecting member rotatably connected to said first end and to be connected to the air supply, and a sleeve rotatably mounted on said connecting member and rigidly connected to said adjusting ring.

12. An end grip member as claimed in claim 11, wherein the rigid connection between said sleeve and said adjusting ring is formed by a detachable connecting structure therebetween.

13. An end grip member as claimed in claim 12, wherein said connecting structure includes elastic flexible tongues formed on said sleeve.

14. An end grip member as claimed in claim 11, wherein said connecting member includes a pipe enveloping a cone attached to said first end.

* * * * *